(12) United States Patent
Blaine et al.

(10) Patent No.: US 11,641,863 B2
(45) Date of Patent: May 9, 2023

(54) METHOD FOR PROCESSING PRODUCTS OF THE FOOD PROCESSING INDUSTRY

(71) Applicants: John Bean Technologies Corporation, Chicago, IL (US); Nordischer Maschinenbau Rud. Baader GmbH + Co. KG, Lübeck (DE)

(72) Inventors: George R. Blaine, Lake Stevens, WA (US); Jon A. Hocker, Bothell, WA (US); Alexander Steffens, Lübeck (DE)

(73) Assignees: John Bean Technologies Corporation, Chicago, IL (US); Nordischer Maschinenbau Rud. Baader GmbH + Co. KG, Lübeck (DE)

( * ) Notice: Subject to any disclaimer, the term of this patent is extended or adjusted under 35 U.S.C. 154(b) by 0 days.

(21) Appl. No.: 16/934,523

(22) Filed: Jul. 21, 2020

(65) Prior Publication Data

US 2020/0345043 A1    Nov. 5, 2020

Related U.S. Application Data

(62) Division of application No. 15/394,208, filed on Dec. 29, 2016, now Pat. No. 10,721,947.

(Continued)

(51) Int. Cl.
*G01N 23/00* (2006.01)
*A23L 3/26* (2006.01)
(Continued)

(52) U.S. Cl.
CPC .............. *A23L 3/263* (2013.01); *A22B 5/007* (2013.01); *A22C 17/008* (2013.01);
(Continued)

(58) Field of Classification Search
None
See application file for complete search history.

(56) References Cited

U.S. PATENT DOCUMENTS

| 4,557,019 A | 12/1985 | Van Devanter et al. |
| 4,748,724 A | 6/1988 | Lapeyre et al. |

(Continued)

FOREIGN PATENT DOCUMENTS

| CA | 233996 A1 | 3/2000 |
| CN | 1303234 A | 7/2001 |

(Continued)

OTHER PUBLICATIONS

Decision to Grant and Search Report dated Nov. 5, 2020, in Russian Application No. 2019104179/10, filed Jul. 27, 2017, 22 pages.

(Continued)

*Primary Examiner* — Hoon K Song
(74) *Attorney, Agent, or Firm* — Christensen O'Connor Johnson Kindness PLLC

(57) ABSTRACT

A method for processing food products (12) includes transporting the food products by a first conveyor (11), an X-ray unit (13) positioned between the intake end and the discharge end of the first conveyor to acquire a first set of product-specific data relating to the food product transported. At least one first optical camera (17), assigned to the first conveyor, is used to acquire a second set of product-specific data relating to the food product. A control unit (18) is used to receive and integrate the first and second data sets to analyze the composition of the food product and determine parameters for the food product. Based on the determined parameters of the food product, the food product is cut with a cutting unit, under the control of the control unit.

17 Claims, 5 Drawing Sheets

Related U.S. Application Data

(60) Provisional application No. 62/368,941, filed on Jul. 29, 2016.

(51) Int. Cl.
*A22C 17/00* (2006.01)
*A22B 5/00* (2006.01)
*G01N 23/04* (2018.01)
*B26D 5/00* (2006.01)
*B26F 3/00* (2006.01)
*G01N 21/27* (2006.01)
*G01N 33/02* (2006.01)

(52) U.S. Cl.
CPC .......... *A22C 17/0086* (2013.01); *B26D 5/007* (2013.01); *B26F 3/004* (2013.01); *G01N 21/27* (2013.01); *G01N 23/04* (2013.01); *G01N 33/02* (2013.01); *B26D 2210/02* (2013.01)

(56) References Cited

U.S. PATENT DOCUMENTS

| | | | |
|---|---|---|---|
| 4,875,254 A | 10/1989 | Rudy et al. | |
| 4,970,757 A | 11/1990 | Heiland et al. | |
| 5,162,016 A | 11/1992 | Malloy | |
| 5,205,779 A | 4/1993 | O'Brien et al. | |
| 5,585,603 A | 12/1996 | Vogeley, Jr. | |
| 5,937,080 A | 8/1999 | Vogeley, Jr. et al. | |
| 6,563,904 B2 | 5/2003 | Wijts et al. | |
| 6,859,282 B1 | 2/2005 | Weber et al. | |
| 6,882,434 B1 | 4/2005 | Sandberg et al. | |
| 7,025,196 B2 | 4/2006 | Pfarr et al. | |
| 7,052,388 B2 | 5/2006 | Houtz | |
| 7,153,203 B2 | 12/2006 | Pfarr et al. | |
| 7,158,915 B2 | 1/2007 | Wargon | |
| 7,251,537 B1 | 7/2007 | Blaine et al. | |
| 7,404,759 B2 | 7/2008 | Sato | |
| 7,452,266 B2 * | 11/2008 | Bottemiller | B26D 7/30 700/173 |
| 7,593,785 B2 | 9/2009 | Blaine et al. | |
| 7,621,806 B2 | 11/2009 | Bottemiller et al. | |
| 7,651,388 B2 | 1/2010 | Faires et al. | |
| 7,672,752 B2 | 3/2010 | Blaine et al. | |
| 7,715,935 B2 | 5/2010 | Vogeley, Jr. et al. | |
| 7,747,042 B2 | 6/2010 | Blaine | |
| 7,857,686 B2 | 12/2010 | Amason | |
| 7,861,630 B2 | 1/2011 | Sorensen et al. | |
| 7,949,414 B2 | 5/2011 | Blaine et al. | |
| 8,096,860 B2 | 1/2012 | Bolte et al. | |
| 8,116,554 B2 | 2/2012 | Burton | |
| 8,147,299 B2 | 4/2012 | McKenna et al. | |
| 8,166,856 B2 | 5/2012 | Kim et al. | |
| 8,351,672 B2 | 1/2013 | Tao et al. | |
| 8,376,814 B2 | 2/2013 | Hattori et al. | |
| 8,412,366 B2 | 4/2013 | Blaine et al. | |
| 8,529,321 B2 | 9/2013 | Weber | |
| 8,643,851 B2 | 2/2014 | Weber | |
| 8,688,259 B1 | 4/2014 | Blaine et al. | |
| 8,688,267 B2 | 4/2014 | Blaine et al. | |
| 8,820,534 B2 | 9/2014 | Thorsson et al. | |
| 8,839,949 B2 | 9/2014 | Vogeley, Jr. | |
| 8,915,773 B2 | 12/2014 | Nielsen | |
| 2002/0067797 A1 * | 6/2002 | Safai | A22C 17/0086 378/54 |
| 2003/0036344 A1 | 2/2003 | Sigurdsson et al. | |
| 2004/0231480 A1 | 11/2004 | Wattles et al. | |
| 2005/0032471 A1 | 2/2005 | Pfarr et al. | |
| 2006/0154587 A1 | 7/2006 | Mikkelsen et al. | |
| 2006/0161380 A1 | 7/2006 | Bottemiller | |
| 2012/0040060 A1 | 2/2012 | Virippil et al. | |
| 2012/0128838 A1 | 5/2012 | Virippil et al. | |
| 2012/0212603 A1 | 8/2012 | Lindee et al. | |
| 2012/0307013 A1 | 12/2012 | Hjalmarsson | |
| 2014/0205739 A1 | 7/2014 | McKenna et al. | |
| 2014/0220193 A1 | 8/2014 | Hocker et al. | |
| 2014/0326644 A1 | 11/2014 | Thorsson et al. | |
| 2015/0033921 A1 | 2/2015 | Finnsson | |
| 2015/0241341 A1 | 8/2015 | Ikeda | |
| 2017/0212506 A1 | 7/2017 | Pfarr et al. | |

FOREIGN PATENT DOCUMENTS

| | | |
|---|---|---|
| CN | 102421297 A | 4/2012 |
| CN | 10272989 A | 10/2012 |
| CN | 102729289 A | 10/2012 |
| CN | 104220348 A | 12/2014 |
| CN | 104700104 A | 6/2015 |
| CN | 104737003 A | 8/2015 |
| DE | 691 04 122 T2 | 3/1995 |
| EP | 1 174 034 A1 | 1/2002 |
| EP | 1 889 542 A1 | 2/2008 |
| EP | 2353305 A1 | 8/2011 |
| EP | 2353395 A1 | 8/2011 |
| EP | 2531038 A1 | 12/2012 |
| EP | 2 878 203 A1 | 6/2015 |
| FR | 2 894 433 A1 | 6/2007 |
| FR | 2 965 619 A1 | 4/2012 |
| GB | 2 285 126 A | 6/1995 |
| GB | 2 364 894 A | 2/2002 |
| GB | 2 405 081 A | 2/2005 |
| JP | 2006208098 A | 8/2006 |
| JP | 2012078303 A | 4/2012 |
| JP | 2016-038364 A | 3/2016 |
| SU | 542140 A1 | 1/1977 |
| WO | 89/008983 A1 | 10/1989 |
| WO | 00/013864 A1 | 3/2000 |
| WO | 2001/032369 A1 | 5/2001 |
| WO | 02/43502 A2 | 6/2002 |
| WO | 02/043502 A2 | 6/2002 |
| WO | 2004/106020 A1 | 12/2004 |
| WO | 2006/064521 A1 | 6/2006 |
| WO | 2006/092311 A1 | 9/2006 |
| WO | 2007/022782 A2 | 3/2007 |
| WO | 2009/102479 A2 | 8/2009 |
| WO | 2010/114397 A1 | 10/2010 |
| WO | 2011095998 A1 | 8/2011 |
| WO | 2011/113081 A1 | 9/2011 |
| WO | 2012/088437 A2 | 6/2012 |
| WO | 2013/155449 A1 | 10/2013 |
| WO | 2013/156159 A1 | 10/2013 |
| WO | 2014/061461 A1 | 4/2014 |
| WO | 2014/100829 A1 | 6/2014 |
| WO | 2014091006 A1 | 6/2014 |
| WO | 2015/003750 A1 | 1/2015 |
| WO | 2015/079039 A1 | 6/2015 |
| WO | 2015/198062 A1 | 12/2015 |

OTHER PUBLICATIONS

Jing, H., "Laser Range Imaging for On-Line Mapping of 3D Images to Pseudo-X-Ray Images for Poultry Bone Fragment Detection," doctoral dissertation, University of Maryland, College Park, 2003, 159 pages.
Machine Translation of the International Search Report and Written Opinion dated Jul. 25, 2017, issued in related International Application No. PCT/EP2017/068737, filed Jul. 25, 2017, 13 pages.
"Waterjet Cutting of Fish Under X-Ray," Food Trade Magazine, Jul. 1, 2012, 2 pages.
Extended European Search Report dated Aug. 30, 3017, issued in corresponding Application No. EP 16207287.0, filed Dec. 29, 2016, 18 pages.
International Search Report and Written Opinion dated Nov. 7, 2017, issued in corresponding International Application No. PCT/US2017/043687, filed Jul. 25, 2017, 12 pages.
International Preliminary Report on Patentability dated Feb. 7, 2019, issued in corresponding International Application No. PCT/US2017/043687, filed Jul. 25, 2017, 9 pages.
International Preliminary Report on Patentability dated Feb. 7, 2019, issued in International Application No. PCT/EP2017/068737, filed Jul. 25, 2017, 18 pages.

(56) References Cited

OTHER PUBLICATIONS

Examination Report dated Sep. 17, 2019, issued in DK Application No. PA 2019 00126 , filed Jul. 25, 2017, 7 pages.
Examination Report dated Oct. 11, 2019, issued in DK Application No. PA 2019 00128, filed Jan. 30, 2019, 8 pages.
Notice of the Reason for Refusal dated Feb. 18, 2020, issued in Japanese Application No. 2019-526365, filed Jul. 25, 2017, 19 pages.
International Search Report and Written Opinion dated Nov. 13, 2017, issued in corresponding International Application No. PCT/US2017/068737, filed Jul. 25, 2017, 12 pages.
Second Office Action dated Jun. 18, 2021, issued in Chinese Patent Application No. 201780047316.8, filed Jul. 25, 2017, 35 pages.
First Office Action with Search Report dated Oct. 30, 2020, issued in Chinese Patent Application No. 201780047316.8, filed Jul. 25, 2017, 39 pages.
Notification of Reason for Refusal dated Aug. 28, 2020, issued in Korean Patent Application No. 20197004668, filed Jul. 25, 2017, 22 pages.
Decision of Refusal dated Sep. 29, 2020, issued in Japanese Application No. 2019-526365, filed Jul. 25, 2017, 13 pages.
First Office Action with Search Report dated Oct. 30, 2020, issued in Chinese Patent Application No. 201780054497.7, filed Jul. 25, 2017, 39 pages.
Second Office Action dated Jun. 18, 2021, issued in Chinese Patent Application No. 201780054497.7, filed Jul. 25, 2017, 35 pages.
Second Office Action dated Jun. 1, 2021, issued in Chinese Patent Application No. 201780047316.8, filed Jul. 25, 2017, 21 pages.
Office Action dated Jul. 5, 2021, issued in Japanese Patent Application No. 2019-526189, filed Jul. 25, 2017, 7 pages.
First Office Action with Search Report dated Sep. 29, 2020, issued in Chinese Patent Application No. 201780047316.8, filed Jul. 25, 2017, 30 pages.
Communication of a Notice of Opposition dated Mar. 1, 2022, issued in European Patent No. 3490383, filed Aug. 7, 2017, 30 pages.
Varzakas, T., and Tzia, C., (eds.), "Handbook of Food Processing: Food Safety, Quality, and Manufacturing Processes," Table of Contents, Preface, and Chapter 14, "Poultry Manufacturing Technologies," by T. Varzakas and V. Feddem, CRC Press, Oct. 2015, 35 pages, and publication data from Google Play, <https"//play.google.com/store/books/details?id=CXq9CgAAQBAJ> [retrieved Feb. 17, 2022], 3 pages.
Larsen, A.B.L., et al., "Vision-Based Method for Tracking Meat Cuts in Slaughterhouses," Meat Science 96(1):366-372, Jan. 2014.
Third Office Action dated Nov. 5, 2021, issued in Chinese Patent Application No. 201780047316.8, filed Jul. 25, 2017, 9 pages.
Decision dated Jan. 27, 2022, issued in Chinese Patent Application No. 201780054497.7, filed Jul. 25, 2017, 26 pages.
Office Action dated Jun. 21, 2022, issued in Korean Patent Application No. KR10-2019-7004810, filed Jul. 25, 2017, 6 pages.

* cited by examiner

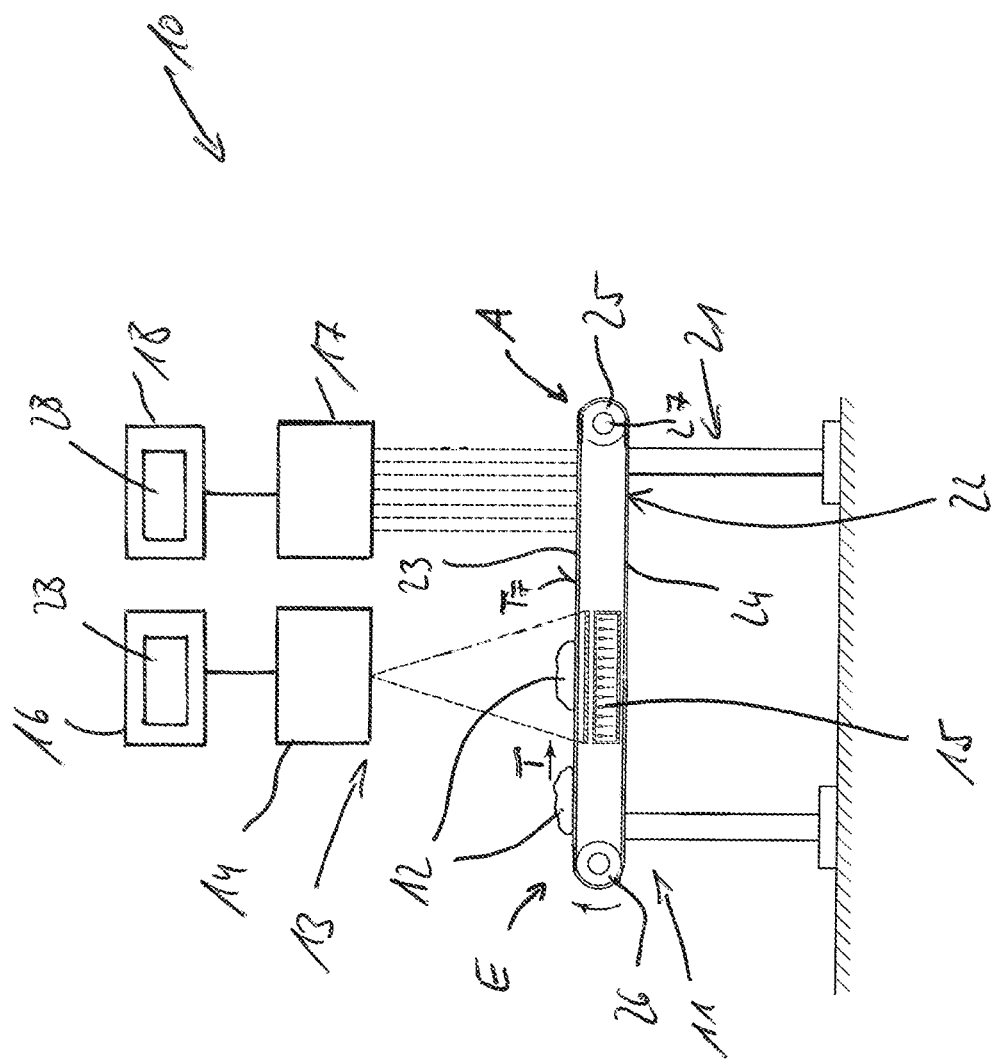

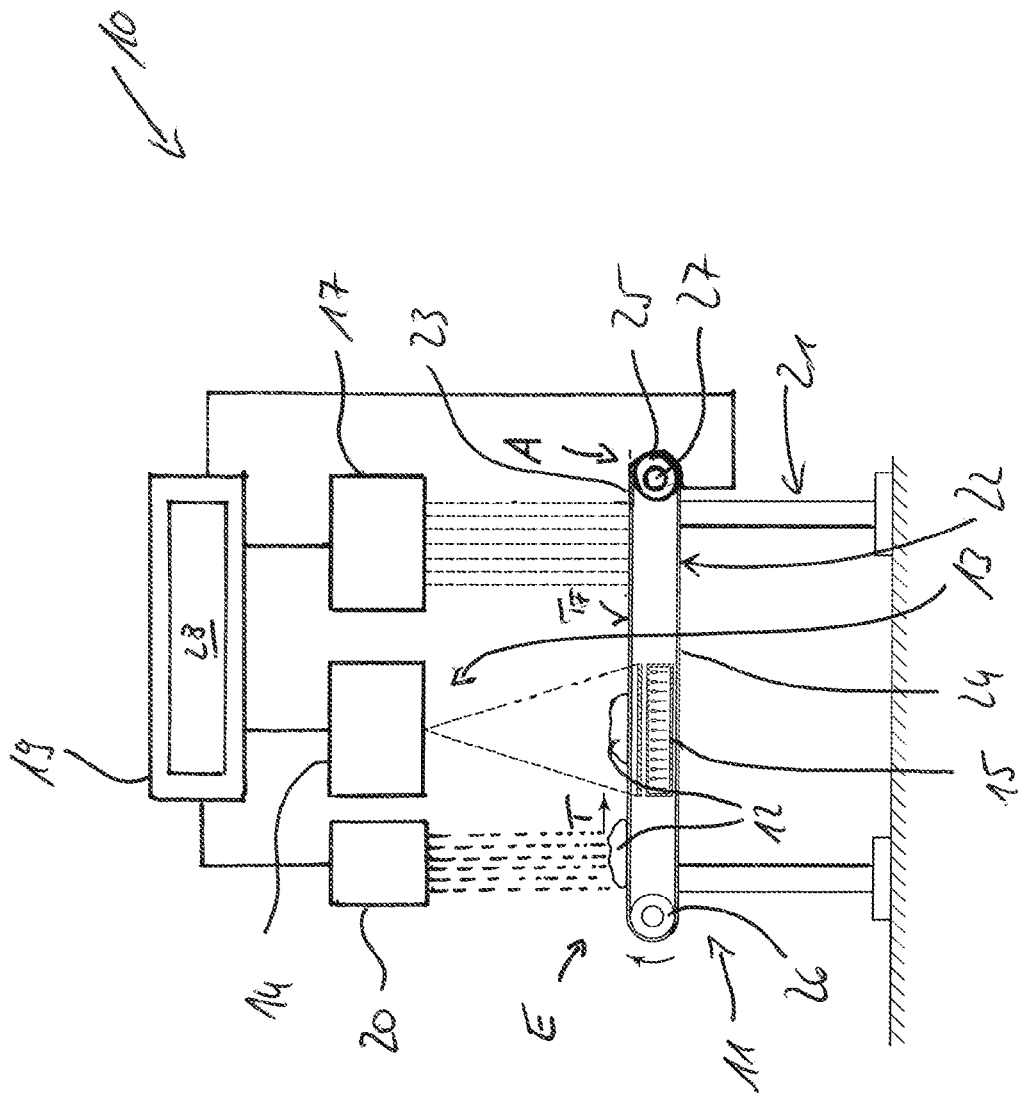

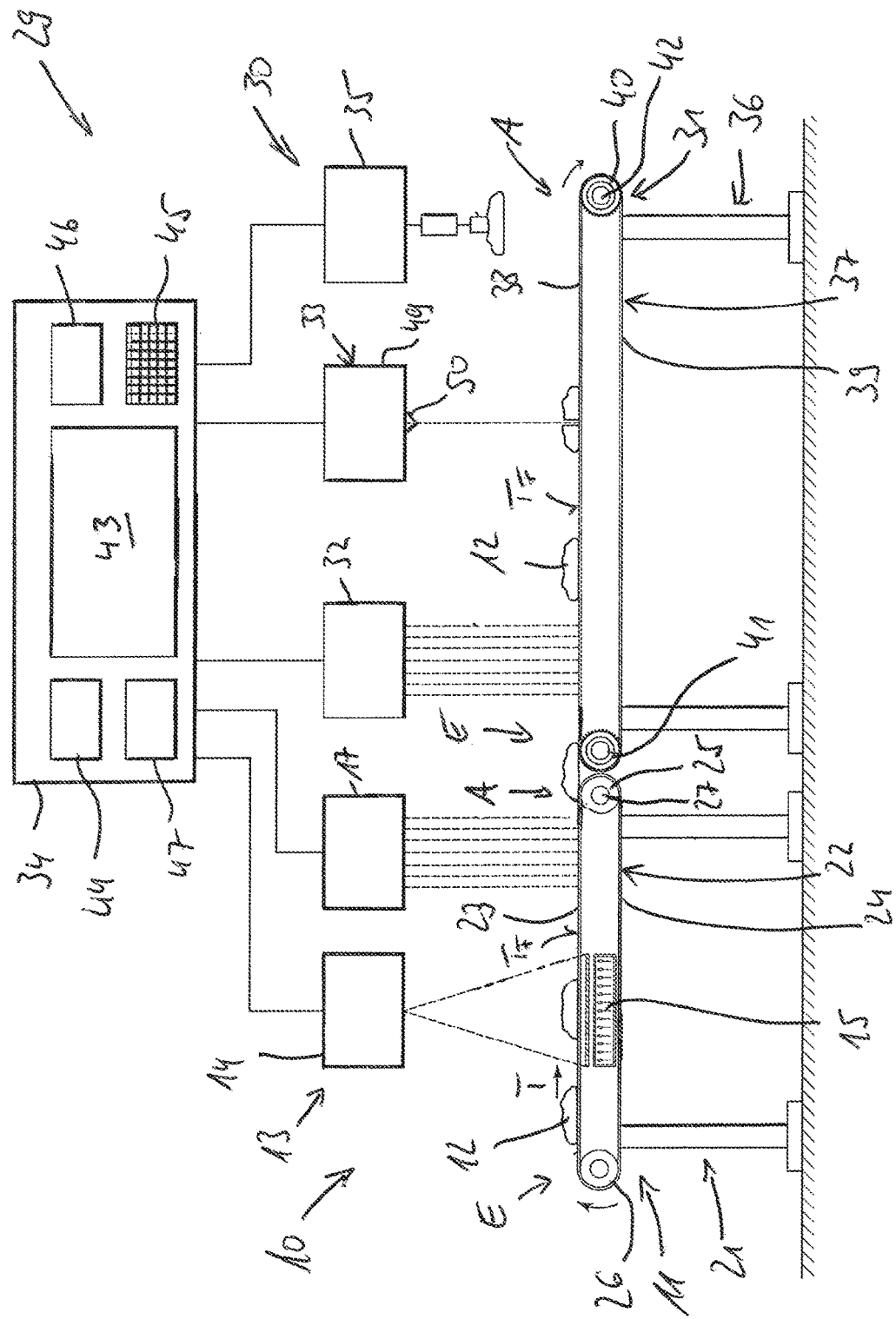

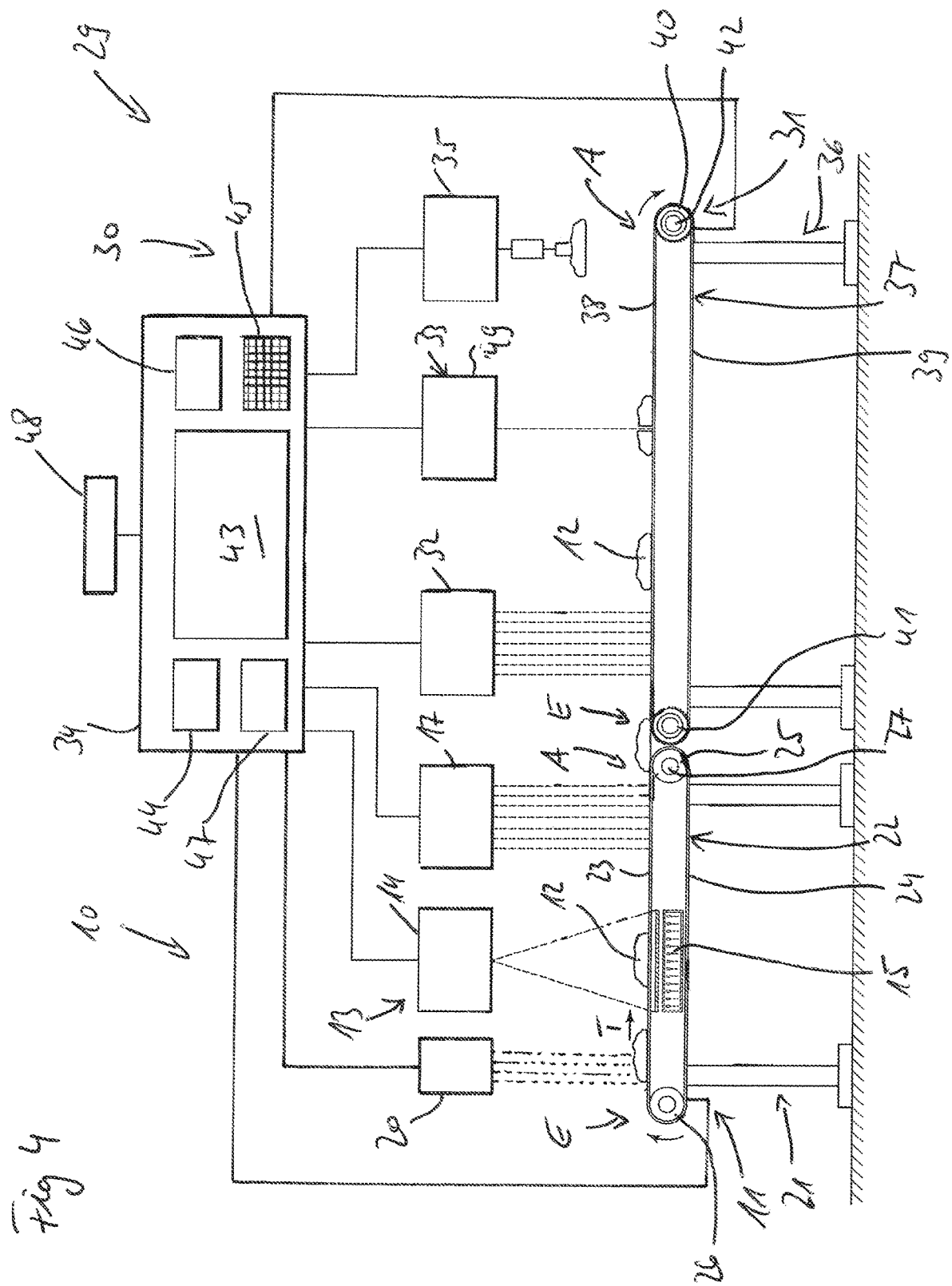

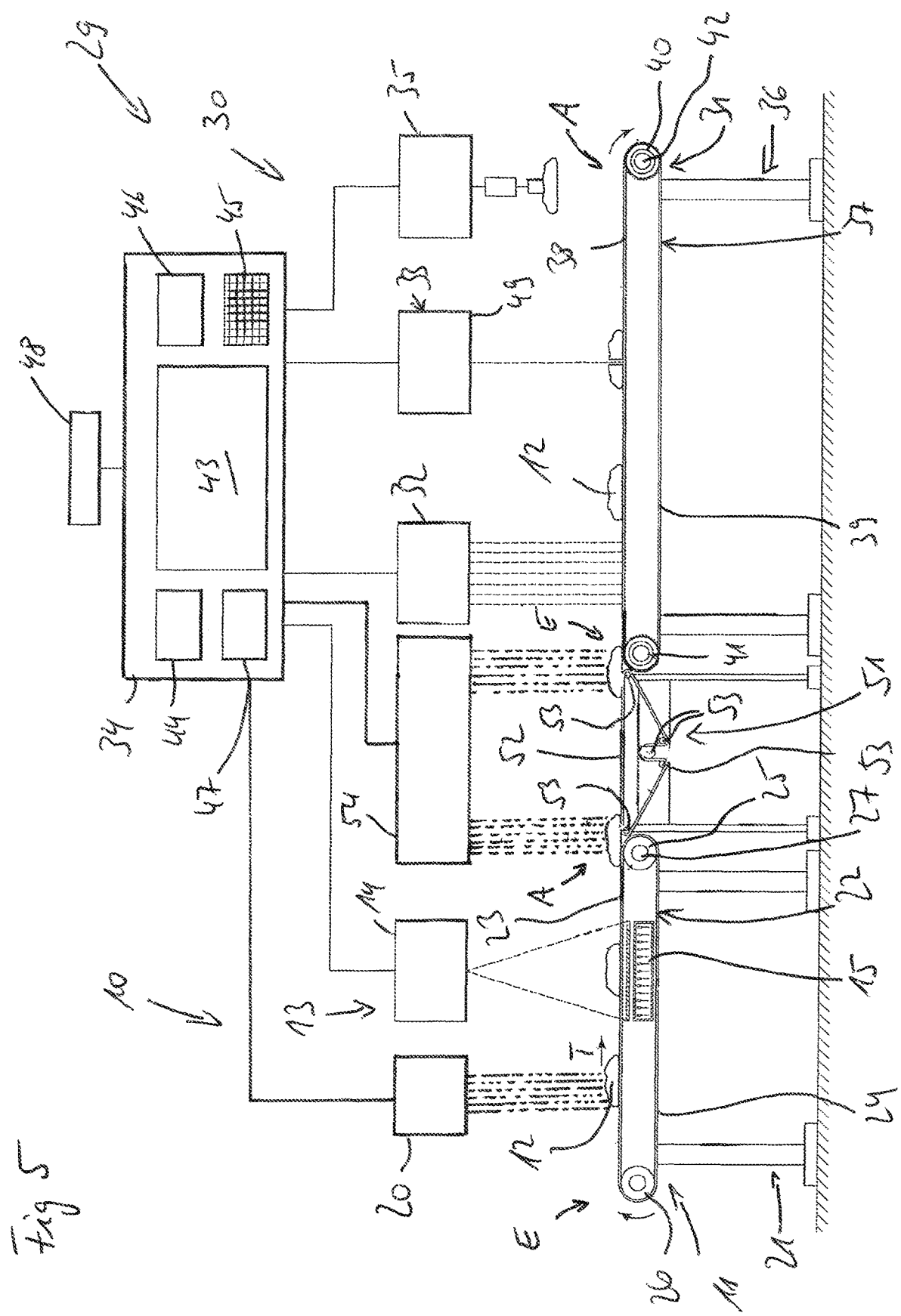

METHOD FOR PROCESSING PRODUCTS OF THE FOOD PROCESSING INDUSTRY

CROSS-REFERENCES TO RELATED APPLICATIONS

This application is a division of U.S. patent application Ser. No. 15/394,208, filed Dec. 29, 2016 (now U.S. patent Ser. No. 10/721,947), which claims the benefit of U.S. Provisional Application No. 62/368,941, filed Jul. 29, 2016, both of which applications are incorporated herein by reference in their entireties.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The invention relates to an apparatus, designed and configured to acquire and analyse product-specific data for products of the food processing industry, comprising a conveyor, which is gap-free in the transport plane, for transporting separated products in transport direction T from an intake end to a discharge end, an X-ray unit having at least one X-ray source and at least one X-ray camera or detector for acquiring product-specific data, wherein X-ray source and X-ray camera are assigned to the conveyor in such a manner that the products can be guided along between the X-ray source and the X-ray camera, as well as a control unit which is connected to the X-ray unit and is designed and configured to receive and analyse the product-specific data, forming a first data set, acquired by said X-ray unit.

The invention further relates to a system, designed and configured to process products of the food processing industry, comprising an apparatus, designed and configured to acquire and analyse product-specific data of the products, as well as a processing station, arranged downstream of the apparatus in transport direction T of the products, which comprises a conveyor for transporting said products in transport direction T from an intake end to a discharge end, at least one optical camera, by means of which the product-specific data of the products transported on the conveyor of the processing station can be acquired, wherein the optical camera is connected to a control unit, which is designed and configured to receive and analyse the product-specific data acquired by the optical camera, as well as a cutting unit which is designed and configured to cut and remove undesirable regions of the products and/or to portion the products, wherein said cutting unit is connected to a control unit for controlling the cutting unit based on the previously acquired product-specific data.

The invention is further aimed at a method for processing products of the food processing industry, comprising the steps: transporting the products using a first conveyor from an intake end to a discharge end in transport direction T, acquiring product-specific data relating to each product on the first conveyor by means of an X-ray unit, wherein the acquired data, forming a first data set, is received by a control unit and is analysed by it in order to define cutting paths for cutting out undesirable regions and/or for portioning, passing the products from the first conveyor to a downstream conveyor by means of which the products are transported in transport direction T from an intake end to a discharge end, acquiring product-specific data relating to each product on the downstream conveyor by means of an optical camera, wherein the acquired data, forming a fourth data set, is received by a control unit and is analysed by it in order to identify each product, matching and analysing the received and analysed data sets by means of a control unit in order to calculate the relative product positions of each product on the two conveyors, and cutting the products along the cutting paths previously determined and assigned to the relevant product by means of a cutting unit, wherein the cutting unit is controlled by a control unit.

Such apparatuses are used particularly in the food processing industry. For many products, it is important for further processing in a downstream station, e.g. sorting, packaging and particularly cutting to remove undesirable regions and/or portioning, to acquire product-specific data. Acquiring product-specific data and information can include, inter alia, acquiring the outer contour, the topography, the external dimensions in length and width, the weight and the thickness, as well as acquiring defects, e.g. in the form of blood spots, bones, bone remnants, bony areas and their position within the product, in addition to tissue structure, etc. Acquiring can be accomplished by detecting, determining, scanning, recording and the like. In previously known apparatuses of the generic type, which are set up exclusively for acquiring product-specific data, an X-ray unit is used for acquiring the product-specific data. The X-ray unit delivers a first data set to the control unit, e.g. an image processing computer (also referred to as CPU). From this data set—in the example case of processing the products by cutting—the control unit is used e.g. to generate cutting paths for the relevant product, e.g. for a bony region to be cut. In addition, the data set determined by the X-ray unit and forwarded to the control unit, can be used e.g. to define the outer contour of the product to be processed. A data set, e.g. for forwarding to a downstream station, is then generated from the outer contour and the cutting paths. In other words, the control unit provides an X-ray image, for example, as a message bearing the information as to the outer contour of the product and where the cutting paths are located.

Use of the X-ray unit requires a conveyor which is as smooth, untextured and gap-free, X-ray transmissive, as possible in order to achieve optimum image quality. In particular, the conveyor is designed to be closed and gap-free in the transport plane. This means that, particularly in the transport plane of the conveyor transverse to transport direction T, a gap which, in product processing apparatuses that are foreign to the classification in question, is configured to hold a cutting means, e.g. a blade and in particular a cutting water jet, is dispensed with to ensure continuous and full-surface support of the products on the conveyor of the apparatus for acquiring and analysing the product-specific data during transport from the intake end to the discharge end. In particular, analysing also includes calculating, converting, etc.

Further processing and particularly matching of the X-ray image provided by the apparatus as a data set with other optical systems, e.g. an optical camera of a downstream processing station, is complex and imprecise due to the different imaging methods. Another problem of known apparatuses is that the detection of more than hard tissue, e.g. bones, bone residues, sinews, etc. of undesirable regions, e.g. blood spots, streaks of fat, parasites, in the products and the detection of outlines, contours and similar can only be achieved imprecisely by the X-ray unit or not at all. In other words, there is a limited area of use for existing apparatuses with an X-ray unit and for the data content of the X-ray image.

This problem is particularly applicable to systems and methods of the food processing industry in which such apparatuses of the type mentioned are used. In the products to be processed, for example poultry fillets or in particular fish fillets, with such systems and methods of the type referred to hereinbefore, individual regions, such as internal bones, fish bones, bony areas or the like, are cut out of the products. Furthermore, other defects, such as blood spots, streaks of fat or the like can also be removed. In addition to cutting undesirable regions off or out of the product, processing of the products also includes portioning them. To detect defects, in particular solid tissue components such as bones and the like, an X-ray unit is provided which is used to identify these defects within the products. For operating the X-ray unit, it is necessary—as mentioned previously—to provide a conveyor which uses a conveyor belt that is as smooth and untextured as possible in order to achieve optimum image quality. For processing the products, in particular cutting by means of a water jet unit, a textured metal mesh belt, which withstands the stresses due to the water jet unit, is useful as the conveyor but is unsuitable for the X-ray unit. Due to the divergent requirements for the conveyors, the known and generic systems have at least two conveyors adjusted to said individual requirements, namely a first conveyor for the apparatus and another for the processing station. This means that the known systems include at least one transfer of the products from a first conveyor to a downstream conveyor. This transfer may result in changes, displacements, twisting, etc. in the orientation/position of the products on the conveyor and, in particular, also to compression and stretching of the products. In spite of this problem, it must be ensured that, after transfer to the conveyor of the processing station, the products are identified and matched in respect of their relative positions on the conveyors so that processing of the products, in particular cutting of the products, can be carried out individually and correctly. In other words, the cutting paths which are determined in relation to a product on the first conveyor are adjusted if necessary for the same product on the second conveyor, or the cutting unit must be adjusted if necessary to the changed position/orientation of the products and therefore the cutting paths must also be adjusted.

On the one hand, with the known systems and methods, tracking of the products is necessary during transport on the conveyors so that the products can be identified or so that the data sets received by the control unit can be assigned. On the other hand, the data sets generated by the X-ray unit must be subjected to matching with the data sets generated by the optical camera of the processing station. For the known systems and methods, for example, the X-ray camera or detector of the X-ray unit transmits its image data to the control unit in image strips. During the X-ray process, every product is conveyed on the conveyor between the X-ray source and the X-ray camera. In the control unit, the image strips received are examined for products. When a product or product piece is present in the image strips, a complete X-ray image of the whole product is generated by putting the image strips together. The product region of the assembled X-ray image is examined for bones or other hard tissue. In a memory of the control unit, data structures are assembled using coordinates of lines which represent the supposed bones. Based on the line data, a bone zone is estimated and from this a cutting path is calculated. This cutting path, also assembled from line segments, is stored that is in coordinates relative to the X-ray image and relative to the position on the conveyor. In the same X-ray image, the control unit is additionally used to determine the outer contour of the product and this is also stored in the form of line segments. A message, that is a first data set, is generated as a transfer image from the outer contour and the or each cutting path. This first data set is forwarded to the control unit of the downstream processing station which can also be the control unit of the system.

After transfer of the product from the first conveyor to the downstream conveyor of the processing station, product-specific data is acquired by means of an optical camera. The acquired data forms a fourth data set. As soon as the processing station has identified and recorded a product, all first data sets previously received and not yet processed are searched by means of the control unit. The first data set with the best match is selected. The fourth data set and the first data set are matched and analysed to identify the products and to calculate the relative product positions of each product on the two conveyors. Numbering of the data sets has no logical or substantive significance but serves the sole purpose of identifying the data sets with respect to their origin.

The known systems and methods have the disadvantage that identification as well as matching and evaluation of the data sets takes place based on different imaging processes, namely the X-ray image (first data set) of the apparatus on the one hand and an optical image (fourth data set) of the processing station on the other hand. In other words, matching takes place by comparing an optical image of the optical camera of the processing station with an X-ray image of the X-ray camera of the apparatus. On the one hand, this matching process is very complex due to the different imaging processes. On the other hand, the necessary precision is lacking during this matching. In other words, the desired and necessary accuracy is missing in the known matching. A further disadvantage is that the X-ray unit cannot identify all the undesirable regions that are to be cut or can only identify them inadequately. In other words, it is difficult for the X-ray unit to identify defects beyond bones, bony areas and other hard tissue. Another disadvantage is that the products have to be tracked during transport through the system which is costly on the one hand and leads to imprecise results on the other hand.

Thus, the object of the invention is to create a simple apparatus by means of which a data set with a higher and more precise data content can be generated. The object further consists of creating an improved system for processing products which enables easier and more precise identification as well as matching and evaluation of the received data sets. The object is also to propose a corresponding method.

This object is addressed by an apparatus having the features referred to hereinbefore in that at least one optical camera is assigned to the same conveyor between its intake end and discharge end, by means of which, in addition to the X-ray unit, product-specific data of the products transported on the conveyor can be acquired, wherein the optical camera is connected to a control unit which is designed and configured to receive and analyse the product-specific data, forming a second data set, acquired by the optical camera. Due to this embodiment according to the invention, the apparatus is able to provide more precise and above all more meaningful data for potential further processing. As a result of the X-ray unit on the one hand and at least one optical camera on the other hand, it is possible to generate more and above all also more accurate data which can be processed in the form of individual, separate data sets or in the form of a data set made up of individual data sets linked together. With the apparatus according to the invention, more exact and more precise image registration becomes possible, which in particular also better represents unevenly distributed compressions/extensions within the products.

At least one optical camera is arranged above the conveyor. This means, for example, that light beams illuminating the product hit the conveyor from above at an angle or hit the product lying on the conveyor such that the camera can pick up the reflected light beams. Simply put, the term "above" means that the camera and optionally the at least one light source are directed obliquely or vertically onto the product from above. An arrangement in which the optical camera is arranged vertically above the conveyor such that, by means of the optical camera, a plan view onto the product is ensured, is particularly advantageous. Of course, an arrangement below the conveyor is also possible.

A development of the apparatus is characterised in that at least two optical cameras, which are equipped with a different imaging process, are assigned to the conveyor. The particularly advantageous aspect of this embodiment is that, for example, a simple optical camera, for example a greyscale camera, can be used to acquire a complete image (photo) of the product for image registration, e.g. the outer contour (as product-specific data) as well as a special camera, for example a multispectral camera, to acquire undesirable regions (as product-specific data), such as blood spots, streaks of fat or the like.

Advantageously, at least one optical camera is accordingly a multispectral or hyperspectral camera. The use of such a camera makes it possible, in addition to the product-specific data that is detectable by the X-ray unit, to acquire further undesirable regions which the X-ray unit in particular can only detect inadequately or not at all in order to optimise the quality of the product-specific data to be acquired.

Accordingly, at least one optical camera is configured as a greyscale camera and/or RGB camera and/or IR and/or UV camera. This embodiment substantially improves the bandwidth of the product-specific data to be acquired and simplifies potential matching with optical images of optical cameras in downstream stations.

The conveyor may be a rotationally driven X-ray conveyor belt made of plastic and low-textured on the transport surface, having a feed belt as the upper run and a return belt as the lower run. The products rest on the transport surface. On the one hand, this transport surface is so smooth, that is to say configured in particular without breaches, openings or the like, that X-ray images can be taken without any interference. On the other hand, the transport surface exhibits slight surface roughness in the millimetre range to prevent the products from slipping/shifting on the conveyor. Accordingly, the transport surface is configured to be low-textured. As already mentioned above, the conveyor has a gap-free transport surface in the transport plane. This means that the products on the transport surface are supported over their entire surface at all times and in all places. In other words, the conveyor with its transport surface of the feed belt forms a continuous support surface for the products. An optimised X-ray image can be ensured as a result.

An exemplary development is characterised in that the conveyor is connected to a control unit which is designed and configured to receive and analyse movement data of said conveyor. Connection of the conveyor to the control unit simplifies assignment of the individual products. In other words, the claimed solution enables improved and more precise assignment of the product-specific data acquired by the X-ray unit and each optical camera to a product. As the X-ray camera and the optical camera are located above the same conveyor and are accordingly very close together, the image data, that is the data sets, can be laid on top of each other without any matching, based directly on the time difference which is dependent on the speed of the conveyor.

In an exemplary embodiment, the X-ray source is arranged above the feed belt and the X-ray camera is arranged between the feed belt and the return belt. With this it is possible to acquire a particularly clear and meaningful X-ray image which improves the identification or acquisition of product-specific data, for example the orientation and position of bones, bony areas and the like within the product.

An exemplary development of the invention is characterised in that the X-ray unit and each optical camera as well as the conveyor are connected to a control unit for receiving and analysing the data sets, wherein the control unit is equipped with at least one processor which is configured to integrate/implement at least portions of the product-specific data of a product acquired by the X-ray unit in the optical image of the optical camera relating to the same product for creating an optical transfer image, forming a third data set. The images or image data generated by the X-ray unit and each optical camera are received by the control unit as data sets and analysed. Particularly advantageously, the first data set (result of the X-ray unit) is integrated/implemented in the second data set (result of the optical camera) such that a third data set is formed. This third data set is an optical transfer image. The orientation/position/extension of bones, bony areas and other hard tissue portions (as product-specific data acquired by the X-ray unit=first data set) is laid over the optical image (=second data set) which, for example, maps the whole product or the outer contour thereof, such that as a result an optical image (=third data set) is created, namely the transfer image. This optical image as the third data set accordingly supplies data about the shape/form of the product, e.g. about the outer contour and about defects, e.g. bony areas, etc. that should be removed. This embodiment makes possible further processing of the product-specific data easier and simpler. Due to the fact that the X-ray unit and the one or more optical camera(s) of the apparatus are assigned to a single conveyor, it is possible to dispense with matching of the images, that is to say the X-ray images and the images from optical cameras. In other words, assignment of the product-specific data to a product is ensured simply and precisely, particularly if the position of the individual products is determinable based on the movement data of the conveyor. The additional optical camera can optionally also supply data about defects which can be acquired and analysed by the control unit.

The development may be characterised in that the control unit with the processor is configured to define cutting paths from the product-specific data acquired by the optical camera and from the product-specific data acquired by the X-ray unit, wherein the cutting paths are defined from the product-specific data of a product acquired by the X- ray unit directly via the optical image of the optical camera relating to the same product, in such a manner that the control unit provides an optical image of an optical camera, namely the transfer image, for further processing. In the event that only a single optical camera is provided in addition to the X-ray unit, by means of the control unit said X-ray unit can provide, for example, only cutting paths while by means of the control unit the optical camera can provide the whole product or the outer contour and if necessary additional cutting paths which supplement the quality of the cutting paths from the X-ray image. These data (cutting paths and product photos and/or outer contour) can then be combined with each other to create a common third data set, namely based on an optical image. In the event that two optical cameras are provided in addition to the X-ray unit, by means of the control unit said X-ray unit can provide, for example, only cutting paths while by means of the control unit the second optical camera provides a product photo and/or the outer contour, and by means of the control unit the second optical camera provides cutting paths.

The apparatus according to the invention can be used as a stand-alone solution. Also, the apparatus may be coupled to a downstream processing station. This means that the knowledge, data, information, etc, obtained from the apparatus described above can be used for further processing in the processing station. This further processing can include sorting, packaging and particularly cutting for the purpose of removing undesirable regions and/or portioning.

The object is accordingly also achieved by a system having the features referred to hereinbefore in that the apparatus, designed and configured to acquire and analyse product-specific data of the products, is configured according to the claims set forth herein. The advantages arising from this have already been described in connection with the apparatus, which is why reference will be made to the relevant passages to avoid repetitions. The fact that optical images from optical cameras can be laid on top of each other for identifying the products is particularly advantageous. In other words, matching is carried out between optical images using the same or at least similar imaging processes so that the quality of the matching process is simplified and improved.

A further aspect of the present disclosure is characterised in that all control units of said system are in operative connection with each other and at least one control unit comprises a processor which is configured to lay optical images of the optical cameras of the apparatus on the one hand and of the processing station on the other hand on top of each other in such a manner that identifying the products and matching the relative positions of each product on the two conveyors of the apparatus on the one hand and of the processing station on the other hand takes place based exclusively on optical images of optical cameras.

In a further aspect of the present disclosure, the apparatus and the processing station are connected to a control unit which comprises a processor that is configured to lay an optical transfer image which is formed from an optical image of an optical camera of the apparatus, enriched by product-specific data acquired by the X-ray unit of said apparatus, and an optical image of the optical camera of the processing station on top of each other in such a manner that the cutting unit can be controlled by the control unit for each product based on individually determined cutting paths. In other words, the third data set and the fourth data set are used for matching.

The cutting unit may comprise a water jet unit having at least one nozzle. This embodiment can be used to carry out particularly fast and precise individual separating and trimming cuts for removing undesirable regions and/or for portioning.

Also, at least one optical camera each in the apparatus on the one hand and in the processing station on the other hand i may be equipped with the same imaging process. This further simplifies matching.

Advantageously, at least one control unit comprises at least one memory, at least one input device and at least one output device.

The object is also achieved by a method having the process steps referred to hereinbefore, in that on the first conveyor, in addition to the product-specific data acquired by the X-ray unit, product-specific data relating to each product is acquired by means of an optical camera, wherein the data acquired by the optical camera assigned to the first conveyor, which form a second data set, is received and analysed by a control unit, and in that identifying the products and matching and analysing the data sets takes place based on the two data sets generated by the optical cameras, namely the second data set and the fourth data set. The advantages arising from this have already been described in connection with the system, which is why reference will be made to the relevant passages to avoid repetitions.

The method is further characterised in that the first data set, which contains cutting paths generated by the X-ray unit, is integrated/implemented in the second data set, namely in the optical image generated by the optical camera assigned to the first conveyor such that an optical transfer image is forwarded to the control unit as a third data set for matching and analysing, wherein identification of the products and matching and analysing of the data sets takes place based on the third and the fourth data set.

The positions of the undesirable regions generated by the X-ray unit are integrated/implemented as vector data, pixel data or the like in the optical image of the optical camera assigned to the first conveyor, and matching and analysing is performed based on the optical image of the optical camera assigned to the first conveyor and the optical image of the optical camera assigned to the second conveyor. Optionally, the undesirable regions generated by a further optical camera of the apparatus can also be integrated/implemented as vector data, pixel data or the like in the optical image which is used for matching.

Advantageously, for identifying the products, every optical image taken with the optical camera assigned to the downstream conveyor is compared to the optical images of the optical camera assigned to the first conveyor, which are stored in a memory of a control unit, and the image with the closest matches is selected.

The method is carried out using a system according to the claims set forth herein.

Further expedient and/or advantageous features and developments as well as process steps emerge from the dependent claims and the description.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 a schematic representation of a first embodiment of the apparatus according to the invention with an X-ray unit and an optical camera, FIG. 2 a schematic representation of a further embodiment of the apparatus according to the invention with an X-ray unit and two optical cameras, FIG. 3 a schematic representation of a first embodiment of the system according to the invention, FIG. 4 a schematic representation of a further embodiment of the system according to the invention, and FIG. 5 a schematic representation of a further embodiment of the system according to the invention.

DETAILED DESCRIPTION

The apparatus illustrated in the drawing is configured to acquire and analyse product-specific data of fish fillets. Accordingly, the system illustrated is configured to process, namely, to cut fish fillets. However, in the same manner, the apparatus and the system are configured to acquire and analyse product-specific data and to process other products of the food processing industry, such as meat, poultry.

FIG. 1 illustrates an apparatus 10 designed and configured to acquire and analyse product-specific data and comprising a conveyor 11, which is gap-free in the transport plane, for transporting separated products 12 in transport direction T from an intake end E to a discharge end A, an X-ray unit 13 having at least one X-ray source 14 and at least one X-ray camera or detector 15 for the acquiring of product-specific data, wherein X-ray source 14 and X-ray camera 15 are assigned to the conveyor 11 in such a manner that the products 12 can be guided along between the X-ray source 14 and the X-ray camera 15. The apparatus 10 also comprises a control unit 16 which is connected to the X-ray unit 13 and is designed and configured to receive and analyse the product-specific data, forming a first data set, acquired by said X-ray unit 13. Thus, the X-ray unit 13 supplies information/data to the control unit 16.

By means of the control unit 16, the product-specific data or portions thereof, such as orientation/position of bones, bony areas acquired by the X-ray unit 13 are analysed and provided as a data set. The connection between the X-ray unit 13 and the control unit 16 can be implemented in different ways, namely e.g. wired/cabled or wireless, e.g. via radio or Bluetooth interfaces or the like.

This apparatus 10 is characterised according to the invention in that at least one optical camera 17 is assigned to the same conveyor 11 between its intake end E and discharge end A, by means of which, in addition to the X-ray unit 13, product-specific data of the products 12 transported on the conveyor 11 can be acquired, wherein the optical camera 17 is connected to a control unit 18 which is designed and configured to receive and analyse the product-specific data, forming a second data set, acquired by the optical camera 17.

By means of the control unit 18, the product-specific data acquired by the optical camera 17, e.g., size and shape of the product, its outer contour, length, width, thickness, profile, weight, among others, but also defects, e.g. blood spots, streaks of fat, among others, or portions thereof are analysed and provided as a second data set. The connection between the optical camera 17 and the control unit 18 can be implemented in different ways, namely e.g. wired/cabled or wireless, e.g. via radio or Bluetooth interfaces or the like.

When taken on their own or in combination with each other, the features and developments as well as the process steps described below illustrate exemplary embodiments. It is expressly pointed out that features and process steps which are summarised in the claims and/or the description and/or the drawing or are described in a common embodiment can also further develop the apparatus described above as well as the system and method described below in a functionally independent manner.

The optical camera 17 can be arranged in transport direction T of the products 12 upstream of the X-ray unit 13 or, as illustrated in FIG. 1, downstream of the X-ray unit 13. The X-ray unit 13 and the optical camera 17 can each be connected to a separate control unit 16, 18. In other embodiments, e.g. according to FIG. 2, the X-ray unit 13 and the optical camera 17 can also be connected to a common control unit 19.

The position of the X-ray unit 13 and/or optical camera 17 can vary in relation to the conveyor 11. In addition to an arrangement of the X-ray unit 13 and/or optical camera 17 below the conveyor 11, an arrangement above the conveyor 11 is perhaps more common. FIG. 1 illustrates such an embodiment by way of example, in which not only the X-ray unit 13 is arranged above the conveyor 11 but also the optical camera 17. Above in this context means that the X-ray source 14 and the light source of the optical camera 17 hit the product 12 from above. This can take place at an oblique angle, including vertically from above in order to obtain a plan view onto the product 12.

In a disclosed embodiment, as illustrated in FIG. 2, at least two optical cameras 17, 20 are assigned to the conveyor 11. The two optical cameras 17, 20 can be equipped with the same imaging process. However, the two optical cameras 17, 20 can be equipped with a different imaging process. Optical cameras within the meaning of the invention can be greyscale cameras/sensors, RGB cameras/sensors and infrared or ultraviolet cameras/sensors. Each optical camera can, for example, be configured as an area scan or line scan camera. With the greyscale cameras or sensors, photoactive components, e.g. photodiode, phototransistor, convert electromagnetic waves in the visible range into electrical signals on a sensor. With the RGB cameras or sensors, the light is divided into a red/green/blue channel depending on location by prefiltering the incoming light waves in front of the pixels. In the infra-red or ultraviolet cameras or sensors, due to selection of the photoactive elements, sensitivity is shifted into the range of the longer wave lengths (IR) or shorter wave lengths (UV) compared to visible light.

At least one of the optical cameras 17, 20 is a multispectral or hyperspectral camera. At least one of the optical cameras 17, 20 is configured as a greyscale and/or RGB camera and/or IR and/or UV camera. In the embodiment according to FIG. 2, one of the optical cameras, for example the optical camera 17, is a simple camera, namely a greyscale camera. By means of this optical camera 17, for example, the outer contour can be acquired as product-specific data and forwarded to the control unit 19. The other optical camera 20 can be a complex camera, namely a hyperspectral camera. By means of the optical camera 20, undesirable regions, e.g. defects in the form of blood spots, bone (residues), cartilage, fat, but also foreign particles, e.g. glass, plastic, etc. can be acquired and forwarded to the control unit 19 as product-specific data. The number of cameras/sensors and their positioning along the conveyor 11 can vary.

The conveyor 11 of the apparatus 10 comprises a frame 21 for supporting a feed belt. The feed belt is a rotationally driven X-ray conveyor belt 22 made of plastic and low-textured on the transport surface $T_F$, having a feed belt 23 as the upper run and a return belt 24 as the lower run. The X-ray conveyor belt 22 with its upwardly facing transport surface $T_F$ is free of openings, breaches, gaps or the like. In other words, the transport surface $T_F$ is configured as closed over the entire length and width. The endlessly configured X-ray conveyor belt 22 which consists of rubber, plastic or another synthetic material and is radiolucent, is guided around at least two deflection elements 25, 26 of which one deflection element 25 or 26 is configured as a drive roller and the other deflection element 26 or 25 as a deflection roller. Particularly in the region of the drive roller, which can be driven by a drive means, an encoder 27 can optionally be provided, by means of which the position of the X-ray conveyor belt 22 can be determined or monitored along the length of the conveyor 11 and therefore the position of the product 12 can be determined or monitored on said conveyor 11. The transport surface $T_F$ of the X-ray conveyor belt 22 directed towards the products 12 is configured to be low-textured. This means that the closed transport surface $T_F$ is slightly roughened. However, completely smooth transport surfaces can also be used.

In the embodiments illustrated in the drawing, the X-ray source 14 is arranged above the conveyor 11 and above the feed belt 23. The X-ray camera 15 is arranged between the feed belt 23 and the return belt 24. Optionally, the X-ray camera 15 can also be arranged below the return belt 24. Other configurations of X-ray source 14 and X-ray camera 15 in relation to the feed belt 23 or return belt 24 are also possible.

Optionally, the conveyor 11 is connected to a control unit 19 which is designed and configured to receive and analyse movement data of said conveyor 11. In the embodiment according to FIG. 2, the conveyor 11 or the encoder 27 is connected to the common control unit 19 to which the X-ray unit 13 and the optical cameras 17, 20 are also connected. Connection to a separate control unit, however, which is in operative connection with the other control units 16, 18, is also possible.

One or each control unit 16, 18, 19 comprises at least one processor (CPU) 28. The X-ray unit 13 and each optical camera 17, 20 as well as the conveyor 11 are connected to a common or superordinate control unit 19 for receiving and analysing the data sets, wherein the control unit 19 is equipped with at least one processor (CPU) 28 which is configured to integrate/implement at least portions of the product-specific data of a product acquired by the X-ray unit 13 in the optical image of the optical camera 17, 20 relating to the same product for creating an optical transfer image, forming a third data set. This embodiment is illustrated in FIG. 2. In other embodiments, only the X-ray unit 13 and/or individual optical cameras 17, 20 and/or the conveyor 11 can be connected to the common control unit 19. The control unit 19 and, if necessary, also each other control unit 16, 18 optionally comprises, in addition to the at least one processor 28, a memory, an input device, an output device and an interface. In addition, it is possible to connect the apparatus 10 via the control unit 19 to a network that can be networked internally (intranet) or externally (Internet). The X-ray unit 13, the optical cameras 17, 20 and the conveyor 11 can also be connected to separate control units 16, 18 which in turn cooperate with a superordinate control unit.

All control units 16, 18, 19 and in particular control unit 19, that is to say an industrial controller, a computer or the like, include as mentioned at least one processor 28 (CPU) which is designed and configured to acquire the data sets from the X-ray unit 13 and each optical camera 17, 20. Selected product-specific data which has been acquired by the X-ray unit 13, for example the orientation of a row of pin bones in a fish fillet (e.g. first data set), is implemented/integrated by means of the processor 28 in the optical image of the optical camera 17, 20 which maps the outer contour of the product 12 (e.g. second data set). In other words, the usable product-specific data from the X-ray unit 13 is laid over the optical image of the optical camera 17, 20. The resulting transfer image (e.g. third data set) is ultimately a data packet with all the data necessary for subsequent processing and obtained from the X-ray unit 13 and each optical camera 17, 20, the transfer image being an optical image.

The control unit 19 with the processor 28 is configured to define cutting paths from the product-specific data acquired by the optical camera 17, 20 and from the product-specific data acquired by the X-ray unit 13, wherein the cutting paths are defined from the product-specific data of a product 12 acquired by the X-ray unit 13 directly via the optical image of the optical camera 17, 20 relating to the same product 12 in such a manner that the control unit 19 provides an optical image of an optical camera 17, 20, namely the transfer image, for further processing. Separate data sets for further processing can also be provided, said data sets being processable by a control unit of a downstream processing station.

Two possible embodiments based on FIGS. 1 and 2 are explained in greater detail purely by way of example. With the apparatus 10 according to FIG. 1, for example, the outer contour of the product 12 can be created or mapped by means of the optical camera 17 and the connected control unit 18 (e.g. second data set), while cutting paths for the regions to be removed from the product 12 can be created by means of the X-ray unit 13 and the connected control unit 16 (e.g. first data set). By overlaying the first data set on the second data set, that is without any matching, the third data set is created or mapped as an optical image. The overlaying can take place, for example, based solely on the time difference determined between generation of the X-ray image and the optical image, that is as a function of the transport speed of the conveyor 11.

With the apparatus 10 according to FIG. 2, for example, the outer contour of the product 12 can be create or mapped by means of the optical camera 17, for example a greyscale camera, and the connected control unit 19. By means of the optical camera 20, for example a hyperspectral camera, and the connected control unit 19, cutting paths can be created or mapped for defects that are not reliably and precisely identified by either the simple optical camera 17 or the X-ray unit 13, namely, blood spots, colour changes, cuts and the like, and which are to be removed from the product 12. From these data sets, the control unit 19 forms a transfer image as the third data set. The transfer image can be created based on the optical image of the greyscale camera and/or based on the optical image of the hyperspectral camera which, in addition to the cutting paths, can also, among other things, create or map the outer contour of the product 12. The transfer image, optionally enriched by the data set provided by the X-ray unit, can then be usable for potential matching with optical images of downstream optical cameras. However, the data set provided by the X-ray unit can also be provided, separately and independently of the data set provided by the one or more camera(s), for further processing.

As already mentioned, the apparatus 10 can be used as a separate and mobile apparatus for acquiring and analysing product-specific data. The apparatus 10 may also be part of a system 29 for processing products 12 of the food processing industry, see FIG. 3. Processing of products 12 includes, in addition to sorting and packaging, in particular also cutting, wherein cutting comprises the removal of undesirable regions of a product 12 on the one hand and/or dividing/portioning of products 12 on the other hand.

The system 29 comprises an apparatus 10, designed and configured to acquire and analyse product-specific data of the products 12, as well as a processing station 30, arranged downstream of the apparatus 10 in transport direction T of the products 12, which comprises a conveyor 31 for transporting said products 12 in transport direction T from an intake end E to a discharge end A, at least one optical camera 32, by means of which the product-specific data of the products 12 transported on the conveyor 31 of the processing station 30 can be acquired, as well as a cutting unit 33. The optical camera 32 is connected to a control unit 34 which is designed and configured to receive and analyse the product-specific data acquired by the optical camera 32. The cutting unit 33 is designed and configured to cut and remove undesirable regions of the products 12 and/or to portion the products 12, wherein the cutting unit 33 is connected to a control unit 34 for controlling the cutting unit 33 based on previously acquired and analysed product-specific data.

This system 29 is characterised according to the invention in that the apparatus 10, designed and configured to acquire and analyse product-specific data of the products 12, is configured in a manner or one of the embodiments is configured in a manner such as that previously described.

FIG. 3 illustrates a first embodiment of the system 29. The apparatus 10 comprises, in addition to the conveyor 11, an X-ray unit 13 and an optical camera 17. The X-ray unit 13 and the optical camera 17 are connected in the embodiment to the control unit 34. Optionally, the conveyor 11 can also be connected to the control unit 34 (see e.g. FIG. 4). All cable/signal connections in the system 29 can be implemented in different ways, namely e.g. wired/cabled or wireless, e.g. via radio or Bluetooth interfaces of the like. The processing station 30 comprises, in addition to the conveyor 31, an optical camera 32 and the cutting unit 33. Optionally, the processing station 30 also comprises a removal station 35 for removing the products 12 or parts thereof from the conveyor 31. Optical camera 32, cutting unit 33 and removal station 35 are connected in the embodiment to the control unit 34. Optionally, the conveyor 31 can also be connected to the control unit 34 (see e.g. FIG. 4). All components can also be connected to separate control units which are in operative connection with a superordinate control unit. It is also possible to link individual or all components of the apparatus 10 to a control unit which for its part is in operative connection with a control unit of the processing station 30.

The conveyor 31 of the processing station 30 has a frame 36 for supporting a feed belt. The feed belt is a rotationally driven conveyor belt 37, having an open or mesh-like structure. The conveyor belt 37 can be made of stainless steel or another robust, rust-free material. The conveyor belt 37 has a feed belt section 38 as the upper run and a return belt section 39 as the lower run. The conveyor belt 37 with its upwardly facing transport surface $T_F$ comprises openings, breaches or the like. In other words, the transport surface $T_F$ is configured over the entire length and width to be permeable, in particular for water. The endlessly configured conveyor belt 37 is guided around at least two deflection elements 40, 41 of which one deflection element 40 or 41 is configured as a drive roller and the other deflection element 41 or 40 as a deflection roller. Particularly in the region of the drive roller, which can be driven by a drive means, an encoder 42 can optionally be provided, by means of which the position of the conveyor belt 37 can be determined or monitored along the length of the conveyor 31 and therefore the position of the product 12 can be determined or monitored on said conveyor 31.

The system 29 according to FIG. 4 is comparable to the system 29 according to FIG. 3 which is why the same reference numbers are used for identical components. In addition to system 29 according to FIG. 3, the system 29 according to FIG. 4 for the apparatus 10 comprises a second optical camera 20 which is also connected to the control unit 34. In addition, the conveyors 11, 31—as already referred to above—are connected to the control unit 34.

For one or each embodiment, all the control units of the system 29 may be in operative connection with each other or form a common control unit 34. This control unit 34 comprises at least one processor 43 which is configured to lay optical images of the optical cameras 17, 20, 32 of the apparatus 10 on the one hand and of the processing station 30 on the other hand on top of each other in such a manner that identifying the products 12 and matching the relative positions of each product 12 on the two conveyors 11, 31 of the apparatus 10 on the one hand and of the processing station 30 on the other hand takes place based exclusively on optical images of optical cameras 17, 20, 32. Optionally, the control unit 34 comprises, in addition to the at least one processor 43, a memory 44, an input device 45, an output device 46 and an interface 47. Furthermore, it is possible to connect the system 29 via the control unit 34 to a network 48 that can be networked internally (intranet) or externally (Internet). By means of the control unit 34 and the processor 43, the image data of the optical images of the apparatus 10 on the one hand and of the processing station 30 on the other hand can thus be compared for identification and they can be matched and analysed to determine the relative positions of each product 12 on the two conveyors 11, 31. By means of the control unit 34, it is additionally possible due to the configuration of the processor 43 to perform transformations between the image data.

In one embodiment, the apparatus 10 and the processing station 30 are connected to a control unit 34 which comprises a processor 43 that is configured to lay an optical transfer image which is formed from at least one optical image of an optical camera 17 and/or 20 of the apparatus 10, enriched by product-specific data acquired by the X-ray unit 13 of said apparatus 10, and an optical image of the optical camera 32 of the processing station 30 on top of each other in such a manner that the cutting unit 33 can be controlled by the control unit 34 for each product 12 based on individually determined cutting paths.

In one embodiment, the cutting unit 33 comprises a water jet unit 49 with at least one nozzle 50. The at least one nozzle 50 is optionally freely controllable in the space so that it can follow any cutting paths. Other cutting means, such as cutting knives, blades, band knives and the like, can also be controlled instead of the water jet unit 49.

At least one optical camera 17, 20, 32 respectively in the apparatus 10 on the one hand and in the processing station 30 on the other hand is equipped with the same imaging process. In a specific embodiment, the apparatus 10 comprises a simple optical camera 17, e.g. a greyscale camera for recording the outer contour, and a complex optical camera 20, e.g. a hyperspectral camera for recording defects, and the processing station 30 comprises a simple optical camera 32, e.g. also a greyscale camera. The mapping can then be performed between two identical imaging systems in a particularly easy manner (greyscale method). In this case, the optical image of the optical camera 17 of the apparatus 10 forms the basis for the transfer image (third data set), in which the data (cutting paths) of the X-ray unit 13 and the second optical camera 20 of the apparatus 10 are incorporated. Matching can also be performed solely on the basis of, for example, the optical image of the optical camera 17, while the data sets of the X-ray unit 13 and the other optical camera 20 are overlaid directly on the optical image of the camera 32 of the processing station 30 to illustrate the cutting paths.

In a further embodiment which is not illustrated, an additional optical camera can be arranged in the transition from conveyor 11 of the apparatus 10 to conveyor 31 of the processing station 30. The optical camera records the discharge end of the conveyor 11 of the apparatus 10 and the intake end of the conveyor 31 of the processing station 30 simultaneously. This optical camera is also connected to the control unit 34. With such an optical camera, it is possible to dispense with matching between two image data (that is image data of the optical camera 32 of the processing station 30 and the optical camera 17 and/or 20 of the apparatus 10) and to calculate a transformation rule by observing the product movement during the transfer from one conveyor 11 to the downstream conveyor 31 by means of the optical camera.

FIG. 5 shows a further embodiment of the system 29 which is basically similar in configuration to the embodiments in FIGS. 3 and 4. System 29 of the embodiment according to FIG. 5, however, comprises an intermediate conveyor 51 between the conveyor 11 of the apparatus 10 and the conveyor 31 of the processing station 30 in order to optimise the transfer of the products 12 from the apparatus 10 to the processing station 30. The intermediate conveyor 51 comprises an endless conveyor belt 52 which is guided around more than two deflection elements 53. At least one of the deflection elements 53 is configured as a drive roller. Further deflection elements 53 are used to adjust the tension of the conveyor belt 52. The deflection elements 53 arranged at the intake end E and discharge end A of the intermediate conveyor 51 are deflection rollers whose external diameters are significantly smaller compared to the external diameters of the deflection elements 25, 41 of the adjacent conveyors 11, 31. As a result, the gap between the conveyor belt 52 and the feed belt 23 on the one side and the feed belt 38 on the other side is reduced such that the conveyor 11 of the apparatus 10, the intermediate conveyor 51 and the conveyor 31 of the processing station form an almost continuous and gap-free transport surface. All conveyors 11, 31 and intermediate conveyor 51 are optimally driven at the same speed. The intermediate conveyor 51 can optionally also equalise an existing height difference between the conveyor 11 of the apparatus 10 and the conveyor 31 of the processing station 30.

The intermediate conveyor 51 is also connected to the control unit 34. In a development of this embodiment, at least one optical camera 54 can be assigned to the intermediate conveyor 51. FIG. 5 shows an option in which the optical camera 54 records both transitions from the conveyor 11 to the intermediate conveyor 51 and from the intermediate conveyor 51 to the conveyor 31. Other arrangements and configurations of the optical cameras are also possible.

Of course, in addition to the particularised optical cameras of system 29 as an imaging system, 3D systems and other imaging systems, for example, can also be used.

The principle of the method is explained in greater detail below based on the drawings.

The method is used for processing products 12 of the food processing industry. It is described for cutting fish fillets. However, the method can also be used in the same way for cutting other products 12, such as chicken fillets or the like, and for sorting or packaging according to product-specific data.

The products 12 are initially transported by means of a first conveyor 11 from an intake end E to a discharge end A in transport direction T. By means of an X-ray unit 13, product-specific data, in particular defects in the form of bones, bony areas and other hard tissue, is acquired in relation to each product 12 on the first conveyor 11, wherein the acquired data, which forms a first data set, is received by a control unit 34 and is analysed by it in order to determine cutting paths for cutting undesirable regions out of the products 12, e.g. out of fish fillets, and/or for portioning of the products 12. The products 12 are then passed from the first conveyor 11 to a downstream conveyor 31 by means of which the products 12 are transported in transport direction T from an intake end to a discharge end. Product-specific data is acquired on the downstream conveyor 31 by means of an optical camera 32, wherein the acquired data, in particular the outer contour, forming a fourth data set, is received by a control unit 34 and is analysed by it in order to identify each product. According to the invention, on the first conveyor 11, in addition to the product-specific data acquired by the X-ray unit 13, product-specific data relating to each product 12 is acquired by means of at least one optical camera 17 and/or 20, wherein the data acquired by the optical camera 17 and/or 20 assigned to the first conveyor 11, which form a second data set, is received and analysed by a control unit 34. In addition, the received data sets are matched and analysed by means of a control unit 34 in order to calculate the relative product positions of each product 12 on the two conveyors 11, 31. Finally, the products 12 are cut along the cutting paths previously determined and assigned to the relevant product 12 by means of a cutting unit 33, wherein the cutting unit 33 is controlled by a control unit 34. The received data sets are further used to perform possible transformations which occur due to displacements, movements, twisting or the like of products 12 during the transfer of said products 12 from one conveyor 11 to another conveyor 31.

As mentioned, there are several options for identifying, and matching and analysing the information collected. Identifying of the products and matching can take place, for example, based solely on the basis of the image of one of the optical cameras 17, 20 of the apparatus 10 and on the basis of the image of the optical camera 32 of the processing station 30. If product 12 is identified and its orientation/position on the second conveyor 31 is known, if necessary after a transformation, the cutting paths, generated from the data sets of the X-ray unit 13 and one of the optical cameras 17, 20 of the apparatus 10, can be integrated/implemented in the image of the optical camera 32 of the processing station 30. Before comparing/matching the image of one of the optical cameras 17, 20 of the apparatus 10 to the image of the optical camera 32 of the processing station 30, the cutting paths, generated from the data sets of the X-ray unit 13 and one of the optical cameras 17, 20 of the apparatus 10, can be integrated/implemented in the image of the further optical camera 17, 20 of the apparatus 10.

Identifying the products 12 and matching and analysing the data sets takes place based on the data sets generated by the optical cameras 17 and/or 20 and 32, namely the second data set and the fourth data set. The received data sets are accordingly also used to map the regions to be removed from the product 12 and/or the cutting lines for portioning the products 12 for the relevant product 12 identified and lying on the conveyor 31 of the processing station 30 in order to control the cutting unit 33.

In other words, according to the invention, an optical image is transmitted from the apparatus 10 to the control unit 34 for matching and this optical image of the apparatus 10 is matched with the optical image of the processing station 30. This means that after processing of all the image data (X-ray image and optical image), which is acquired from the products 12 on the first conveyor 11, said data is transmitted to the control unit 34 (CPU) for the matching process. These image data individual to each product 12 are stored in a list. After each product 12 on the second conveyor 31 has been acquired by means of the optical camera 32, the optical image of the optical camera 32 is compared to the image data from the list. The image or images which display the closest matches are selected from the list. After successful matching of the optical image of the optical camera 32 with an image/image data from the list, this image/these image data are removed from the list. In other words, for identifying the products 12, every optical image taken with the optical camera 32 assigned to the downstream conveyor 31 is compared to the optical images of the optical camera 17 and/or 20 assigned to the first conveyor 11, which are stored in a memory 44 (also referred to as a list) of a control unit 34, and the image with the closest matches is selected. After successful identifying and, if necessary, matching and analysing, the relevant optical image is deleted from the memory.

If no (appropriate) image/no (appropriate) image data is present in the list or in the memory 44 respectively, or if no image/no image data from the memory 44 achieves an adequate matching result, the product 12 can be skipped in the processing and be transported, for example, to manual processing. If an image/image data remains in the memory 44 longer than feasible, it can optionally be removed automatically from the memory 44.

The first data set, which contains cutting paths generated by the X-ray unit 13, is integrated/implemented in the second data set, namely in the optical image generated by the optical camera 17 or 20 assigned to the first conveyor 11 such that an optical transfer image is forwarded to the control unit 34 as a third data set for matching and analysing, wherein identification of the products 12 and matching and analysing of the data sets takes place based on the third and the fourth data set. This means that the image data of the optical camera 17 or 20 (together with the data obtained from the X-ray unit 13) is transmitted to the control unit 34. In addition, the control unit 34 receives the image data of the optical camera 32 and processes all the image data after assignment to a product 12 to control the cutting unit 33. Optionally, the data of the X-ray unit 13, the image data of the optical camera 17 or 20 and the image data of the optical camera 32 can be transmitted separately to the control unit 34. The data of the X-ray unit 13 can then be overlaid over the image data of the optical camera 32 of the processing station 30. Subsequently, it is possible to perform a comparison of the image data of the optical camera 17 or 20 of the apparatus 10 to the image data of the optical camera 32 of the processing station 30 to ensure that the product 12 is the identical product. The, if necessary, transformation of the data of the X-ray unit 13 and/or the optical camera 17, 20 of the apparatus 10, e.g. by X-Y translation, rotation, X-Y shear, X-Y displacement or the like, from the optical image of the camera 17 or 20 of the apparatus 10 to the optical image of the camera 32 of the processing station 30 can take place. The sequence of these steps can vary.

Matching itself can be performed, for example, as explained below: Distinctive points are searched for in the optical images of the optical camera 17 or 20 and 32 and based on their relative orientation to one another they are assigned such that relative orientations/proximities are mapped as well as possible. In this case, a transformation function is determined which maps a rectangular grid over the optical image of the optical camera 17 or 20 of the apparatus 10 to a spline-shaped grid over the optical image of the optical camera 32 of the processing station 30. By means of the transformation function, an unambiguous point in the coordinate system of the optical image of the optical camera 32 of the processing station 30 is assigned to each point in the coordinate system of the optical image of the optical camera 17 or 20 of the apparatus 10. The matching result is determined via the similarity of all the image data of the product 12 in the image data of the optical cameras 17 or 20 and 32, wherein the transformation function is used to assign the points to each other. Similarity in this case is to be understood in the sense of the smallest possible deviations with respect to the relevant imaging process.

The positions of the undesirable regions generated by the X-ray unit 13 and/or a further optical camera 17, 20 are integrated/implemented as vector data, pixel data or the like in the optical image of the optical camera 17, 20 assigned to the first conveyor 11, wherein matching and analysing is performed based on the optical image of the optical camera 17, 20 assigned to the first conveyor 11 and the optical image of the optical camera 32 assigned to the second conveyor 31. Thus, it is possible that, in addition to identifying (e.g. via the outer contour of the product), the optical image will also be used for generating cutting paths.

The method described is performed with a system 29 such as that described above.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for processing food products, comprising:
   (a) transporting the food products by a first conveyor having an intake end and a discharge end;
   (b) using an X-ray unit positioned between the intake end and the discharge end of the first conveyor to acquire product-specific data specific to the X-ray unit detection of each food product transported over the entirety of the food product being transported on the first conveyor, wherein the product-specific data specific to X-ray detection acquired over the entirety of the food product forms a first data set;
   (c) using at least one first optical camera assigned to the first conveyor to acquire additional product-specific data specific to the optical camera detection of each food product over the entirety of the food product, wherein the product-specific data specific to optical camera detection acquired over the entirety of the food product forms a second data set;
   (d) using a control unit to receive the first and second data sets and integrate over the entirety of the food product the first and second data sets for each food product to analyze the composition of the food product and determine parameters for the food product; and
   (e) based on the determined parameters of the food product, cutting the food product with a cutting unit, wherein the cutting unit is controlled by the control unit.

2. A method for processing food products, comprising:
   (a) transporting the food products by a first conveyor having an intake end and a discharge end;
   (b) using an X-ray unit positioned between the intake end and the discharge end of the first conveyor to acquire product-specific data relating to the food product transported on the first conveyor, wherein the acquired product-specific data forms a first data set;
   (c) using at least one first optical camera assigned to the first conveyor to acquire additional product-specific data of each food product, wherein the data acquired by the at least one first optical camera forms a second data set;

(d) using a control unit to receive the first and second data sets and integrate the first and second data sets to analyze the composition of the food product and determine parameters for the food product;

(e) based on the determined parameters of the food product, cutting the food product with a cutting unit, wherein the cutting unit is controlled by the control unit;

(f) passing the food products from the first conveyor to a downstream conveyor;

(g) acquiring product-specific data relating to the food product on the downstream conveyor by means of a downstream optical camera, wherein the acquired data, forming a fourth data set, is received by the control unit and is analyzed by the control unit to identify the food product;

(h) matching and analyzing the received and analyzed data sets by means of the control unit to calculate the relative positions of each food product on the first and second conveyors; and (i) the control unit identifying the products and matching and analyzing the data sets based on the two data sets generated by the at least one first optical camera and the downstream optical camera.

3. The method according to claim 2, wherein the first data set is integrated in the second data set, namely in the optical image generated by the at least one first optical camera such that an optical transfer image is forwarded to the control unit as a third data set for matching and analyzing, wherein identification of the food products and matching and analyzing the data sets takes place based on the third and fourth data sets.

4. The method of claim 2, further comprising cutting the food product to accomplish at least one objective selected from the group of removing undesirable regions of the food product and portioning the food product.

5. The method according to claim 4, wherein positions of the undesirable regions generated by the X-ray unit and/or at least one first optical camera are integrated as vector data or pixel data in the optical image of the at least one first optical camera, and that matching and analyzing is performed based on the optical image of the at least one first optical camera and the optical image of the downstream optical camera.

6. The method according to claim 2, wherein for identifying food products, the optical image taken with the downstream optical camera is compared to the optical images of the at least one first optical camera, and the image of the at least one first optical camera with the closest match is selected.

7. The method according to claim 1, further comprising placing the first optical camera above the first conveyor.

8. The method according to claim 1, utilizing two first optical cameras which are equipped with a different imaging process.

9. The method according to claim 1, further comprising operable interconnecting the first conveyor to the control system, the control system receiving and analyzing the movement of the first conveyor based on data received from the first conveyor.

10. The method of claim 1, further comprising:
connecting the X-ray unit and each of the first optical cameras to the control unit for receiving and analyzing the first and second data sets; and
using the control unit to integrate at least portions of the food product-specific data acquired by the X-ray unit in the optical image of the at least one first optical camera relating to the same food product to create an optical transfer image, forming a further data set.

11. The method of claim 10, wherein:
the control unit determines cutting paths from the food-specific data acquired by the at least one first optical camera and from the food-specific data acquired by the X-ray unit; and
defining the cutting paths from the food-specific data acquired by the X-ray unit directly via the optical image of the at least one first optical camera relating to the same food product in such a manner that the control unit provides an optical image of the at least one first optical camera, namely, the optical transfer image for further processing.

12. The method of claim 1, further comprising cutting the food product by the cutting unit to accomplish at least one objective selected from the group of removing undesirable regions of the food product and portioning the food product.

13. A method for processing food products, comprising the steps:
transporting the food products by means of a first conveyor from an intake end to a discharge end,
acquiring product-specific data relating to each food product on the first conveyor by means of an X-ray unit, wherein the acquired data, forming a first data set, is received by a control unit and analysed by the control unit to define cutting paths for cutting out undesirable regions of the food product and/or for portioning,
passing the food products from the first conveyor to a downstream conveyor by means of which the food products are transported in transport direction from an intake end to a discharge end of the downstream conveyor,
acquiring product-specific data relating to each food product on the downstream conveyor by means of a downstream optical camera, wherein the acquired data, forming a fourth data set, is received by the control unit and is analysed by it in order to identify each food product,
matching and analysing the received and analysed data sets by means of the control unit in order to calculate the relative positions of each food product on the first and downstream conveyors, and
cutting the food products along the cutting paths previously determined and assigned to the relevant food product by means of a cutting unit, wherein the cutting unit is controlled by the control unit,
wherein for the first conveyor, in addition to the food product-specific data acquired by the X-ray unit, additional product-specific data relating to each food product is acquired by means of at least one first optical camera assigned to the first conveyor, wherein the data acquired by the at least one first optical camera, which forms a second data set, is received and analysed by the control unit, and wherein identifying the products and matching and analysing the data sets takes place based on the two data sets generated by the downstream conveyor and the at least one first optical cameras, namely the second data set and the fourth data set.

14. The method according to claim 13, wherein the first data set, which contains cutting paths generated by the X-ray unit, is integrated/implemented in the second data set, namely in the optical image generated by the at least one first optical camera such that an optical transfer image is forwarded to the control unit as a third data set for matching and analyzing, wherein identification of the food products and matching and analyzing of the data sets takes place based on the third and the fourth data sets.

15. The method according to claim 13, wherein positions of the undesirable regions generated by the X-ray unit and/or the at least one first optical camera are integrated/implemented as vector data or pixel data in the optical image of the at least one first optical camera, and that matching and analyzing is performed based on the optical image of the at least one first optical camera and the optical image of the downstream optical camera.

16. The method according to claim 13, wherein for identifying the food products, the optical images taken with the downstream optical camera are compared to the optical images of the at least one first optical camera, which are stored in a memory of a control unit, and the image of the at least one first optical camera with the closest match is selected.

17. A method for processing food products, comprising:
(a) transporting the food products by a first conveyor having an intake end and a discharge end;
(b) using an X-ray unit positioned between the intake end and the discharge end of the first conveyor to acquire product-specific data specific to the X-ray unit detection of each food product transported on the first conveyor, wherein the acquired product-specific data forms a first data set;
(c) using at least one first optical camera assigned to the first conveyor to acquire additional product-specific data specific to the optical camera detection of each food product over the entirety of each food product, wherein the data acquired by the least one first optical camera comprises the size and shape of each food product and forms a second data set;
(d) using a control unit to receive the first and second data sets and integrate over the entirety of the food product the first and second data sets for each food product to analyze the composition of the food product and determine parameters for the food product; and
(e) based on the determined parameters of the food product, cutting the food product with a cutting unit, wherein the cutting unit is controlled by the control unit.

* * * * *